(12) United States Patent
Henzler et al.

(10) Patent No.: US 7,981,633 B2
(45) Date of Patent: Jul. 19, 2011

(54) METHOD FOR MEASURING TYROSINE KINASE PHOSPHORYLATION

(75) Inventors: Tanja Henzler, Schriesheim (DE); Bjoern Hock, Maintal (DE); Andree Blaukat, Muehltal (DE); Uwe Hofmann, Seeheim-Jugenheim (DE)

(73) Assignee: Merck Patent GmbH, Darmstadt (DE)

( * ) Notice: Subject to any disclaimer, the term of this patent is extended or adjusted under 35 U.S.C. 154(b) by 23 days.

(21) Appl. No.: 11/995,742

(22) PCT Filed: Jul. 7, 2006

(86) PCT No.: PCT/EP2006/006642
§ 371 (c)(1),
(2), (4) Date: Jan. 15, 2008

(87) PCT Pub. No.: WO2007/009613
PCT Pub. Date: Jan. 25, 2007

(65) Prior Publication Data
US 2008/0206800 A1    Aug. 28, 2008

(30) Foreign Application Priority Data
Jul. 16, 2005  (EP) .................................... 05015493

(51) Int. Cl.
*C12Q 1/48* (2006.01)
(52) U.S. Cl. ........................................ 435/15; 435/7.94
(58) Field of Classification Search ................... 435/15, 435/194, 7.1, 7.94
See application file for complete search history.

(56) References Cited

U.S. PATENT DOCUMENTS

| | | | | |
|---|---|---|---|---|
| 6,355,636 | B1 * | 3/2002 | Wissner et al. ............ | 514/234.5 |
| 7,189,694 | B2 | 3/2007 | Johnson et al. | |
| 2007/0059785 | A1 * | 3/2007 | Bacus et al. ................. | 435/7.23 |
| 2008/0026485 | A1 * | 1/2008 | Hueber et al. ................ | 436/507 |
| 2009/0170125 | A1 * | 7/2009 | Heit et al. .................... | 435/7.4 |

FOREIGN PATENT DOCUMENTS
WO    WO 2004094463 A2    11/2004

OTHER PUBLICATIONS

Bonetta Laura Probing the Kinome Nature Methods 2(3)225-232, Mar. 2005.*
Dahring T K et al, "Inhibition of growth factor-mediated tyrosine phosphorylation in vascular smooth muscle by PD 089828 a new synthetic protein tyrosine kinase inhibitor", The Journal of Pharmacology and Experimental Therapeutics Jun. 1997, vol. 281 No. 3, Jun. 1997, pp. 1446-1456, XP002409611.
Boutahar Nadia et al, "Mechanical strain on osteoblasts activates autophosphorylation of focal adhesion kinase and proline-rich tyrosine kinase 2 tyrosine sites involved in ERK activation", The Journal of Biological Chemistry Jul. 16, 2004, vol. 279 No. 29, Jul. 16, 2004, pp. 30588-30599, XP002409612.
Roy Sashwati et al, "Dermal wound healing is subject to redox control", Molecular Therapy: The Journal of the American Society of Gene Therapy Jan. 2006, vol. 13 No. 1, Jan. 2006, pp. 211-220, XP002409613.

* cited by examiner

*Primary Examiner* — Ralph Gitomer
(74) *Attorney, Agent, or Firm* — Millen, White, Zelano, Branigan, P.C.

(57) ABSTRACT

The present invention relates to methods for measuring the autophosphorylation of one or more tyrosine kinases and use of such methods in profiling kinase inhibitors and activators. As a representative example, the method comprises inducing kinase autophosphorylation activity in cells in presence and in absence of a kinase inhibitor, lysing the cells, capturing the tyrosine kinase in the cell lysate by adding a plurality of tyrosine kinase specific binding proteins which are associated with unique dyes, adding a phosphotyrosine specific antibody tagged with a marker which is distinguishable from the unique dyes, and identifying the autophosphorylated tyrosine kinase by detecting the unique dye and the marker. Alternately, the tyrosine kinases themselves could be coupled to the unique dyes. The present invention also relates to kits and compositions for carrying out the above-described methods.

16 Claims, 3 Drawing Sheets

METHOD FOR MEASURING TYROSINE KINASE PHOSPHORYLATION

FIELD OF THE INVENTION

The invention relates to an immuno assay for the detection of autophosphorylation of up to 100 different tyrosine kinases in one cavity.

BACKGROUND OF THE INVENTION

With the availability of a burgeoning sequence database, genomic applications demand faster and more efficient methods for the global screening of protein expression in cells. However, the complexity of the cellular proteome expands substantially if protein post-translational modifications are also taken into account.

Dynamic post-translational modification of proteins is important for maintaining and regulating protein structure and function. Among the several hundred different types of post-translational modifications characterized to date, protein phosphorylation plays a prominent role. Enzyme-catalyzed phosphorylation and dephosphorylation of proteins is a key regulatory event in the living cell. Complex biological processes such as cell cycle, cell growth, cell differentiation, and metabolism are orchestrated and tightly controlled by reversible phosphorylation events that modulate protein activity, stability, interaction and localization. Perturbations in phosphorylation states of proteins, e.g. by mutations that generate constitutively active or inactive protein kinases and phosphatases, play a prominent role in oncogenesis. Comprehensive analysis and identification of phosphoproteins combined with exact localization of phosphorylation sites in those proteins ('phosphoproteomics') is a prerequisite for understanding complex biological systems and the molecular features leading to disease.

Protein phosphorylation represents one of the most prevalent mechanisms for covalent modification. It is estimated that one third of all proteins present in a mammalian cell are phosphorylated and that kinases, enzymes responsible for that phosphorylation, constitute about 1-3% of the expressed genome. Organisms use reversible phosphorylation of proteins to control many cellular processes including signal transduction, gene expression, the cell cycle, cytoskeletal regulation and apoptosis. A phosphate group can modify serine, threonine, tyrosine, histidine, arginine, lysine, cysteine, glutamic acid and aspartic acid residues. However, the phosphorylation of hydroxyl groups at serine (90%), threonine (10%), or tyrosine (0.05%) residues are the most prevalent, and are involved among other processes in metabolism, cell division, cell growth, and cell differentiation. Because of the central role of phosphorylation in the regulation of life, much effort has been focused on the development of methods for characterizing protein phosphorylation. Many of these phosphorylation sites regulate critical biological processes and may prove to be important diagnostic or therapeutic targets for molecular medicine. For example, of the more than 100 dominant oncogenes identified to date, 46 are protein kinases.

Many cancers are characterized by disruptions in cellular signaling pathways that lead to uncontrolled growth and proliferation of cancerous cells. Receptor tyrosine kinases (RTKs) play a pivotal role in these signaling pathways, transmitting extracellular molecular signals into the cytoplasm and/or nucleus of a cell. Cells of virtually all tissue types express transmembrane receptor molecules with intrinsic tyrosine kinase activity through which various growth and differentiation factors mediate a range of biological effects (reviewed in Aaronson, Science 254: 1146-52 (1991).

The catalytic activity of tyrosine kinases is frequently stimulated by autophosphorylation within a region of the kinase domain termed the activation segment (Weinmaster et al. (1984) Cell 37, 559-568), and indeed this has been viewed as the principal mechanism through which RTKs are activated (Hubbard and Till (2000) Annu. Rev. Biochem. 69, 373-398 and Hubbard, (1997) EMBO J. 16, 5572-5581). Structural analysis of the isolated kinase domains of several receptors has revealed how the activation segment represses kinase activity, and the means by which phosphorylation releases this autoinhibition. In the case of the inactive insulin receptor, Tyr 1162 in the activation segment protrudes into the active site, and the activation segment blocks access to the ATP-binding site (Hubbard et al., (1994) Nature 372, 746-754). Autophosphorylation of Tyr 1162 and two adjacent tyrosine residues repositions the activation segment, thereby freeing the active site to engage exogenous substrates and reorganizing the residues required for catalysis into a functional conformation (Hubbard (1997) EMBO J. 16, 5572-5581). In contrast, the activation segment of the fibroblast growth factor (FGF) receptor is relatively mobile and the tyrosines, which become phosphorylated upon receptor activation, do not occupy the active site. However, the C-terminal end of the FGFR1 activation segment appears to block access to substrate (Mohammadi et al. (1996) Cell 86, 577-587).

Receptor tyrosine kinases within the scope of the present invention include but are not limited to epidermal growth factor receptor (EGFR), PDGF receptor, insulin receptor tyrosine kinase (IRK), Met receptor tyrosine kinase, fibroblast growth factor (FGF) receptor, insulin receptor, insulin growth factor (IGF-1) receptor, TrkA receptor, TIE-1, Tek/Tie2, Flt-1, Flk, VEGFR3, EGFR (HER-1, ERBB2 (HER-2), ERBB3 (HER-3), ERBB4 (HER-4), Ret, Kit, Alk, AxI1, FGFR1, FGFR2, FGFR3 and Eph receptors.

Biological relationships between various human malignancies and disruptions in growth factor-RTK signal pathways are known to exist. For example, overexpression of EGFR-family receptors is frequently observed in a variety of aggressive human epithelial carcinomas, such as those of the breast, bladder, lung and stomach (see, e.g., Neal et al., Lancet 1: 366-68 (1985); Sainsbury et al., Lancet 1: 1398-1402 (1987)). Similarly, overexpression of HER2 has also been correlated with other human carcinomas, including carcinoma of the stomach, endometrium, salivary gland, bladder, and lung (see, e.g. Yokota et al., Lancet 1: 765-67 (1986); Fukushigi et al., Mol. Cell. Biol. 6: 955-58 (1986)). Phosphorylation of such RTKs activates their cytoplasmic domain kinase function, which in turns activates downstream signaling molecules. RTKs are often phosphorylated at multiple different sites, such as distinct tyrosine residues. These enzymes are gaining popularity as potential drug targets for the treatment of cancer. For example, Iressa™, an inhibitor of EGFR, has recently entered clinical trials for the treatment of breast cancer. Similarly, Gleevec™, an inhibitor of BCR/ABL, is now widely used for the treatment of CML. The great advantage of targeted therapeutics, which seek to alter the activity of a single protein, over conventional chemotoxic or radiation therapies is, that they specifically target the deregulated cell and therefore, should not have the wide cytotoxicity and adverse side effects seen with current therapies. Abnormal proliferation, differentiation, and/or dysfunction of cells are considered to be the cause of many diseases. Protein kinases and related molecules play an important role in controlling these cells so that they are very important drug targets.

Protein kinases are critical components of cellular signaling cascades that control cell proliferation and other responses to external stimuli. Modulating these signaling cascades through the inhibition of kinases has the potential to impact many diseases and conditions, including cancer, inflammation, diabetes, and stroke.

Cancer is the second leading cause of death in the western world. Despite advances in diagnosis and treatment, overall survival of patients remains poor. Scientific advances in recent years have enhanced our understanding of the biology of cancer. Human protein tyrosine kinases (PTKS) play a central role in human carcinogenesis and have emerged as the promising new targets. Several approaches to inhibit tyrosine kinase have been developed. These agents have shown impressive anticancer effects in preclinical studies and are emerging as promising agents in the clinic. The remarkable success of BCR-ABL tyrosine kinase inhibitor imatinib (Gleevec™) in the treatment of chronic myeloid leukaemia has particularly stimulated intense research in this field. At least 30 inhibitors are in various stages of clinical development in cancer, and about 120 clinical trials are ongoing worldwide. Innovative approaches are needed to fully evaluate the potential of these agents, and a concerted international effort will hopefully help to integrate these inhibitors in cancer therapy in the near future.

As a result, protein kinases have become one of the most prominent target families for drug development. Hence, there is an urgent need to develop newer more effective therapies to improve patient outcomes.

Rapid scientific advances in recent years have enhanced our understanding of the biology of cancer. Consequently, several novel targets have been identified. Tyrosine kinases have emerged as a new promising target for cancer therapy. Many small molecule kinase inhibitors are currently in development, and the approvals of Gleevec™ (Novartis; leukemia, gastrointestinal tumors) and Iressa™ (AstraZeneca; lung cancer) have validated the inhibition of kinases as a highly promising therapeutic strategy.

Human genome sequence analysis has identified about 518 human protein kinases (constituting about 1.7% of all the human genes). Within this large protein kinase complement, at least 90 tyrosine kinase genes have been identified (58 receptor tyrosine kinases (RTKS, Table 1) and 32 nonreceptor tyrosine kinases (NRTKS, Table 2). The cell signalling pathways they initiate are complex (Schlessinger J. et al. Cell 103 (2000), pp. 211-225). In brief, receptor tyrosine kinases (RTKs) contain an amino-terminal extracellular ligand-binding domain (usually glycosylated), a hydrophobic transmembrane helix, and a cytoplasmic domain, which contains a conserved protein tyrosine kinase core and additional regulatory sequences (that contain crucial C-terminal tyrosine residues and receptor regulatory motifs). Ligand binding (HGF, IGF, EGF, TGF-, or others) to the extracellular domain (ECD) results in receptor dimerisation/oligomerisation, leading to activation of cytoplasmic tyrosine kinase activity and phosphorylation of tyrosine residues (Schlessinger et al., Neuron (1992) 9:383-391). Autophosphorylated tyrosine residues serve as a platform for the recognition and recruitment of a specific set of signal-transducing proteins (such as proteins containing SH2 (Src homology 2) and PTB (phosphotyrosine binding) domains) that modulate diverse cell signalling responses. Nonreceptor tyrosine kinases have a common conserved catalytic domain (similar to RTKs) with a modular N-terminal, which has different adapter protein motifs. Tyrosine kinases play a critical role in the regulation of fundamental cellular processes including cell development, differentiation, proliferation, survival, growth, apoptosis, cell shape, adhesion, migration, cell cycle control, T-cell and B-cell activation, angiogenesis, responses to extracellular stimuli, neurotransmitter signalling, platelet activation, transcription, and glucose uptake (Hunter T. Philos. Trans. R. Soc. Lond., B Biol. Sci. 353 (1998), pp. 583-605). Given their pivotal role in normal homeostasis, it is perhaps not surprising that they have been implicated in several human disorders including developmental anomalies (craniosynostosis syndromes and others), immunodeficiency (severe combined immunodeficiency disease (SCID), hereditary agammaglobulinaemia), non-insulin-dependent diabetes mellitus (NIDDM), atherosclerosis, psoriasis, renal disease, neurological disorders, leukaemia, and solid tumors (Madhusudan S, and Ganesan T S. Clin Biochem. 2004 July; 37(7):618-35).

TABLE 1

Receptor tyrosine kinases and cancer

| Tyrosine kinase | Cancer associations |
|---|---|
| EGFR family | |
| EGFR (HER-1) | Breast, ovary, lung, glioblastoma multiforme, and others |
| ERBB2 (HER-2) | Breast, ovary, stomach, lung, Colon, and others |
| ERBB3 (HER-3) | Breast |
| ERBB4 (HER-4) | Breast, granulosa cell tumors |
| Insulin R family | |
| IGF-1R | Cervix, kidney (clear cell), sarcomas, and others |
| IRR, INSR | — |
| PDGFR family | |
| PDGFR-a | Glioma, glioblastoma, ovary |
| PDGFR-β | Chronic myelomonocytic leukaemia (CMML), glioma |
| CSF-1R | CMML, malignant histiocytosis, glioma, endometrium |
| KIT/SCFR | GIST, AML, myelodysplasia, mastocytosis, seminoma, lung |
| FLK2/FLT3 | Acute myeloid leukaemia (AML) |
| VEGFR family | |
| VEGFR1 | Tumor angiogenesis |
| VEGFR2 | Tumor angiogenesis |
| VEGFR3 | Tumor angiogenesis, Kaposi sarcoma, haemangiosarcoma |
| FGFR family | |
| FGFR-1 | AML, lymphoma, several solid tumors |
| FGFR-2 | Stomach, breast, prostate |
| FGFR-3 | Multiple myeloma |
| FGFR-4 | — |
| KLG/CCK family (CCK4) | — |
| NGFR family | |
| TRKA | Papillary thyroid cancer, neuroblastoma |
| TRKB | |
| TRKC | Congenital fibrosarcoma, acute myeloid leukaemia |
| HGFR family | |
| MET | Papillary thyroid, rhabdomyosarcoma, liver, kidney |
| RON | Colon, liver |
| EPHR family | |
| EPHA2 | Melanoma |
| EPHA1, 3, 4, 5, 6, 7, and 8 | — |
| EPHB2 | Stomach, oesophagus, colon |
| EPHB4 | Breast |
| EPHB1, 3, 5, and 6 | — |

TABLE 1-continued

Receptor tyrosine kinases and cancer

| Tyrosine kinase | Cancer associations |
|---|---|
| AXL family | |
| AXL | AML |
| MER, TYRO3 | — |
| TIE family | |
| TIE | Stomach, capillary haemagioblastoma |
| TEK | Tumor angiogenesis |
| RYK family (RYK) | Ovarian cancer |
| DDR family (DDR1 and DDR2) | Breast, ovarian cancer |
| RET family (RET) | Thyroid (papillary and medullary), multiple endocrine neoplasia |
| ROS family (ROS) | Glioblastoma, astrocytoma |
| LTK family | |
| ALK | non-Hodgkin lymphoma |
| LTK | — |
| ROR family (ROR1 and ROR2) | — |
| MUSK family (MUSK) | — |
| LMR family (AATYK, AATYK 2, and 3) | — |
| RTK106 | — |

TABLE 2

Nonreceptor tyrosine kinases and cancer

| Tyrosine kinase | Cancer associations |
|---|---|
| ABL family | |
| ABL1 | Chronic myeloid leukaemia (CML), AML, ALL, CMML |
| ARG | AML |
| FRK family | |
| BRK | Breast |
| FRK | — |
| SRMS | — |
| JAK family | |
| JAK1 | Leukaemias |
| JAK2 | AML, ALL, T-cell childhood ALL, atypical CML |
| JAK3 | Leukaemia, B-cell malignancies |
| JAK4 | — |
| SRC-A family | |
| FGR | AML, CLL, EBV-associated lymphoma |
| FYN | — |
| SRC | colon, breast, pancreas, neuroblastoma |
| YES1 | colon, melanoma |
| SRC-B family | |
| BLK | — |
| HCK | — |
| LCK | T-cell ALL, CLL |
| LYN | — |
| SYK family | |
| SYK | Breast |
| ZAP70 | — |
| FAK family | |
| FAK | adhesion, invasion and metastasis of several tumors |
| PYK2 | adhesion, invasion and metastasis of several tumors |

TABLE 2-continued

Nonreceptor tyrosine kinases and cancer

| Tyrosine kinase | Cancer associations |
|---|---|
| ACK family | |
| ACK1 | — |
| TNK1 | — |
| CSK family | |
| CSK | — |
| MATK | — |
| FES family | |
| FER | — |
| FES | — |
| TEC family | |
| BMX | — |
| BTK | — |
| ITK | — |
| TEC | — |
| TXK | — |

Tyrosine kinases play a central role in oncogenic transformation of cells. This is achieved in several ways (Blume-Jensen P. et al. Nature 411 (2001), pp. 355-365). Gene amplification and/or overexpression of PTKs (e.g., EGFR and HER-2 overexpression that is commonly seen in several cancers) cause enhanced tyrosine kinase activity with quantitatively and qualitatively altered downstream signalling. Genomic rearrangements (like chromosomal translocation) can result in fusion proteins with constitutively active kinase activity (e.g., p210BCR-ABL fusion protein seen in chronic myeloid leukaemia). Gain of function (GOF) mutations or deletion in PTKs within the kinase domain or extracellular domain result in constitutively active tyrosine kinase (e.g., EGFRvll mutant that lacks amino acids 6-273 of the extracellular domain is constitutively active and is seen in solid tumors). Autocrine-paracrine stimulation by overexpression of ligands results in persistent tyrosine kinase stimulation (e.g., TGF- is overexpressed in glioblastoma and head and neck cancer (Grandis J. R. et al. J. Cell. Biochem. 69 (1998), pp. 55-62). Finally, retroviral transduction of a protooncogene corresponding to a PTK concomitant with deregulating structural changes is a frequent mechanism by which oncogenic transformation occurs in animals (rodents and chicken) (Blume-Jensen P. et al. Nature 411 (2001), pp. 355-365).

A significant number of tyrosine kinases (both receptor and nonreceptor types) are associated with cancers. Clinical studies suggest that overexpression/deregulation of tyrosine kinases may be of prognostic/predictive value in patients (i.e., may indicate an aggressive tumor biology or may predict poor response to therapy and shorter survival). EGFR family of tyrosine kinases is the most widely investigated. EGFR (HER-1) overexpression is associated with a poor prognosis in ovarian, head and neck, oesophageal, cervical, bladder, breast, colorectal, gastric, and endometrial cancer (Nicholson R. I et al. Eur. J. Cancer 37 Suppl. 4 (2001), pp. S9-S15). HER-2 overexpression is associated with poorer outcome in patients with breast (Tandon A. K. et al. A. K. Clin. Oncol. 7 (1989), pp. 1120-1128), ovary Meden H. et al. Eur. J. Obstet. Gynecol. Reprod. Biol. 71 (1997), pp. 173-179), prostate (Sadasivan R. et al. J. Urol. 150 (1993), pp. 126-131), lung (Selvaggi G. et al. Cancer 94 (2002), pp. 2669-2674) and bone cancer (Zhou H. et al. J. Pediatr. Hematol. Oncol. 25 (2003), pp. 27-32). Mutation in C-KIT tyrosine kinase is associated with inferior survival in patients with gastrointestinal stromal tumors (Taniguchi M. et al. Cancer Res. 59

(1999), pp. 4297-43) and adversely affects relapse rate in acute myeloid leukaemia (Care R. S. et al. Br. J. Haematol. 121 (2003), pp. 775-777). In small cell lung cancer, C-KIT expression was linked to poor survival (Naeem M. et al. Hum. Pathol. 33 (2002), pp. 1182-1187). The expression of IGF-1R along with IGF-1 and IGF-2 may have prognostic value in a subset of colorectal cancer patients (Peters G. et al. Virchows Arch. (2003). In acute myeloid leukaemia, FLT 3 mutation predicts higher relapse rate and a shorter event free survival (Schnittger S. et al. Blood 100 (2002), pp. 59-66). VEGF is a central growth factor that drives tumor angiogenesis and is an important prognostic marker in solid tumors (Fox S. B. et al. Lancet Oncol. 2 (2001), pp. 278-289). Recent studies suggest that VEGFR 3 expression in lung cancer is associated with a significantly lower survival rate (Arinaga M. et al. Cancer 97 (2003), pp. 457-464) and in colorectal cancer, it may have prognostic significance (Parr C. et al. Int. J. Oncol. 23 (2003), pp. 533-539). Trk tyrosine kinase is an important marker for neuroblastoma (NB). TrkA is present in NB with favourable biological features and highly correlated with patient survival, whereas TrkB is mainly expressed on unfavourable, aggressive NB with MYCN-amplification (Eggert A. et al. Klin. Padiatr. 212 (2000), pp. 200-205). HGFR (Met) overexpression is associated with disease progression, recurrence, and inferior survival in early-stage invasive cervical cancer (Baycal C. et al. Gynecol. Oncol. 88 (2003), pp. 123-129) correlates with poor prognosis in synovial sarcoma (Oda Y. et al. Hum. Pathol. 31 (2000), pp. 185-192) and predicts a significantly shorter 5-year survival in hepatocellular carcinoma (Ueki T. et al. Hepatology 25 (1997), pp. 862-866). Axl tyrosine kinase expression was associated with poor outcome in acute myeloid leukaemia (Rochlitz C. et al. Leukemia 13 (1999), pp. 1352-1358). Tie-1 kinase expression inversely correlates with survival in gastric cancer (Lin W. C. et al. Clin. Cancer Res. 5 (1999), pp. 1745-1751) and in early chronic phase chronic myeloid leukaemia (Verstovsek S. et al. Cancer 94 (2002), pp. 1517-1521). Soluble Tie-2 receptor levels independently predict loco-regional recurrence in head and neck squamous cell (Horner J. J. et al. Head Neck 24 (2002), pp. 773-778). ALK protein expression is an independent predictor of survival and serves as a useful biologic marker of a specific disease entity within the spectrum of anaplastic large cell lymphoma (ALCL, Gascoyne R. D. et al. Blood 93 (1999), pp. 3913-3921). Src tyrosine kinase is an independent indicator of poor clinical prognosis in all stages of human colon carcinoma (Aligayer H. et al. Cancer 94 (2002), pp. 344-351). BCR-ABL tyrosine kinase is of prognostic value and predicts response to therapy in haematological malignancies including chronic myeloid leukaemia (Olavarria E. et al. Blood 97 (2001), pp. 1560-1565 and O'Dwyer M., et al. Oncologist 7 Suppl. 1 (2002), pp. 30-38) and acute lymphoblastic leukaemia (Gleissner B. et al. Blood 99 (2002), pp. 1536-1543) FAK overexpression is correlated with tumor invasiveness and lymph node metastasis in oesophageal squamous cell carcinoma (Miyazaki, T. et al. Br. J. Cancer 89 (2003), pp. 140-145) and reduced expression of the Syk gene is correlated with poor prognosis in breast cancer (Toyama T. et al. Cancer Lett. 189 (2003), pp. 97-102).

Several approaches to target tyrosine kinases have been developed. Tyrosine kinase domain inhibitors, tyrosine kinase receptor blockers (e.g., monoclonal antibodies), ligand modulators (e.g., monoclonal antibodies), RNA interference and antisense technology, gene therapy strategy, inhibitors of Src tyrosine kinase, BCR-ABL inhibitors, downstream signal transduction pathway inhibitor are potential strategies for cancer therapy. Classification of such inhibitors based on their mode of action is summarized in Table 3.

Receptor tyrosine kinases are multidomain proteins. The catalytic domain (Mg-ATP complex binding site) has emerged as the most promising target for drug design in recent years. Random screening of compound libraries initially identified small molecule chemical inhibitors of the catalytic domain. Combinatorial chemistry, in-silico cloning, structure-based drug design, and computational chemistry have now become indispensable tools in lead compound identification and optimisation of these inhibitors. Highly sensitive, accurate, and reliable high throughput assays for screening inhibitors have been developed (including scintillation proximity assay, fluorescence polarisation assay, homogenous time-resolved fluorescence assay, and the heterogeneous time-resolved dissociation-enhanced fluorescence technology (F. A. Al-Obeidi and K. S. Lam, Oncogene 19 (2000), pp. 5690-5701). Knowledge about tertiary structure of protein kinases has expanded, and the X-ray crystallographic structure for over 50 protein kinases has been resolved. Understanding of the molecular interactions of the various parts of the 'ATP-binding site' (adenine region, sugar region, hydrophobic pocket, hydrophobic channel, and the phosphate-binding region) has accelerated drug development (Fabbro D. et al. Pharmacol. Ther. 93 (2002), pp. 79-98).

TABLE 3

Classification of inhibitors

| Small molecule inhibitors | Ligand modulation |
| --- | --- |
| Targeting EGFR | Targeting VEGF |
| ZD1839 (Iressa, Gefitinib) | Bevacizumanb (RhuMAb, Avastink) |
| OSI-774 (Tarceva, Erlotinib, CP-358774) | MV833 |
| | Soluble Flt-1 and Flk-1 |
| PKI-166 | VEGF Trap |
| CI-1033 (PD183805) | GFB 116 |
| CGP-59326A | NM3 |
| EKB-569 | VEGF 121-diphtheria toxin |
| GW 572016 | conjugate |
| Targeting HER-2/neu | Targeting EGF |
| PKI-166 (also inhibits EGFR) | DAB389EGF (diphtheria toxin conjugate) |
| TAK165 | Targeting FGF |
| GE-572016 (inhibits EGFR) | Interferon-a (reduces FGF production) |
| CI-1033 (pan erbB inhibitor) | |
| Targeting VEGFR | Monoclonal antibodies against receptors |
| SU5416 (also targets FLT3) | |
| ZD4190 | Targeting EGFR |
| PTK787/ZK222584 | IMC-C225 (Cetuximab) |
| CGP 41251 | ABX-EGF |
| CEP-5214 | Y10 |
| ZD6474 (also inhibits RET) | MDX-447 (EMD 82633) |
| BIBF1000 | h-R3 |
| VGA1102 | EMD 72000 |
| SU6668 (also inhibits PDGFR and FGFR) | Targeting HER-2/neu |
| | Herceptin (trastuzumab) |
| Targeting PDGFR | MDX-H210 |
| SU11248 (also inhibits C-KIT, FLT-3) | 2C4 (pertuzumab) |
| | Targeting VEGFR |
| CGP-57148 | IMC-1C11 (anti-KDR antibody) |
| Tricyclic quinoxalines (also targets C-KIT) | Anti-Flt-1 antibody (MF1) |
| Targeting FGFR | Gene therapy approaches |
| SU4984 | Targeting EGFR |
| SU5406 | Antisense oligonucleotide |
| Targeting BCR-ABL | Targeting VEGF/VEGFR |
| STI571 (Glivec) (also targets C-KIT, PDGFR) | Antisense oligonucleotides |
| | Adenovirus-based Flt-1 gene therapy |
| NSC680410 | Retrovirus-based Flk-1 gene therapy |
| Targeting C-KIT | Retrovirus-based VHL gene therapy |
| PD166326 (also targets BCR-ABL) | Angiozyme |
| | Targeting IGF-1R |
| PD1173952 (also targets BCR-ABL) | INX-4437 (Antisense oligonucleotides) |

TABLE 3-continued

Classification of inhibitors

| Small molecule inhibitors | Ligand modulation |
|---|---|
| Targeting FLT3 | Others |
| CT53518 | APC8024 (vaccine against HER-2 |
| GTP14564 | overxpressing cells) |
| PKC412 | AP22408 (Src SH2 domain inhibitor) |
| Targeting Src | B43-genistein conjugate |
| PP1 (also inhibits C-KIT, BCR-ABL) | AG538 (IGF-1R inhibitor) |
| PD116285 | |
| CGP77675 | |
| CGP76030 | |
| Targeting TRK | |
| CEP-701 (also inhibits Flt 3) | |
| CEP2583 | |

Although ATP-binding site is highly conserved among tyrosine kinases, minor differences in kinase domain architecture have allowed development of highly selective inhibitors (Levitzki A. Eur. J. Cancer 38 Suppl. 5 (2002), pp. S11-S18). Data on EGFR co crystallised with its inhibitor OSI-774 (Tarceva™) were published recently and provide valuable insight into the mechanism of action of this compound (Stamos J. at al. J. Biol. Chem. 277 (2002), pp. 46265-46272). Most small molecules in clinical development bind in the vicinity of the ATP-binding site of their target kinases, using a part of their scaffold to mimic the binding of the adenine moiety of ATP. Such ATP mimics are competitive inhibitors of the substrate-binding sites within the catalytic domain (Laird A. D. et al. Expert Opin. Invest. Drugs 12 (2003), pp. 51-64 and Fry D. W. Exp. Cell Res. 284 (2003), pp. 131-139) and compete with endogenous ATP (often present in millimolar levels in cells) for binding. Early potent lead compounds had poor solubility and required extended multiple dosing schedules to achieve and maintain adequate plasma levels in patients necessary for optimal target inhibition. To increase solubility, new compounds were generated, but they had reduced affinity to the kinase domain. To circumvent these problems, irreversible inhibitors are now being developed in the hope that covalent attachment of a selective inhibitor to the kinase domain would completely abolish catalytic activity and would translate into potent drugs (Denny W. A. et al. Pharmacol. Ther. 93 (2002), pp. 253-261). Two such inhibitors are in advanced stage of development (CI-1033) (Pfizer) and EKB-569 (Wyeth) that bind irreversibly to EGFR and HER-2, respectively (Laird A. D. et al. Expert Opin. Invest. Drugs 12 (2003), pp. 51-64). Small molecules that target more than one tyrosine kinase have also been developed, and they have the potential to block multiple pathways and produce enhanced anticancer effect (Table 3). PKI-166 inhibits EGFR and HER-2 (Mellinghoff I. K. et al. Cancer Res. 62 (2002), pp. 5254-5259CI-1033) is a pan ErbB inhibitor (Slichenmyer, W. J. et al. Semin. Oncol. 28 (2001), pp. 80-85), SU6668 inhibits VEGFR, PDGFR, and FGFR (Hoekman K. et al. 7 Cancer J. Suppl. 3 (2001), pp. S134-S13, and STI 571 inhibits BCR-ABL, C-KIT, PDGFR, and ARG (Buchdunger, E. et al. Eur. J. Cancer 38 Suppl. 5 (2002), pp. S28-S36. and Nishimura N. et al. Oncogene 22 (2003), pp. 4074-4082.

In the 1980s, first natural tyrosine kinase inhibitors quercetin and genistein were reported (Akiyama T. et al. J. Biol. Chem. 262 (1987), pp. 5592-5595 and J. Mendelsohn J. J. Clin. Oncol. 20 (2002), pp. 1S-13S). Since then, an overwhelming number of natural and synthetic small molecules inhibitors have been described. Tyrosine kinase inhibitors can be broadly categorised into natural products and related derivatives (quercetin, genistein, staurosporine, erbastatins, clavilactones); quinazolines, pyridopyrimidines, and related heterocyles (e.g., ZD1839); phenylamino-pyrimidines (e.g., STI 571); tryphostins and analogues (e.g., SU1498, SU101, SU0020); indoles and oxindoles (e.g., SU5416, SU6668, SU5402; F. A. Al-Obeidi and K. S. Lam, Oncogene 19 (2000), pp. 5690-5701).

One of the major difficulties in the development of small molecule kinase inhibitors is specificity (McMahon et al. (1998) Curr. Op. in Drug Discovery and Dev. 1(2), 131-146). Most compounds currently target the highly conserved ATP binding site of kinases, and therefore tend to bind and inhibit more than one enzyme in the class. Because there are more than 500 human protein kinases (Manning et al., Science (2002) 298, 1912) and inhibition of multiple kinases (or the "wrong" kinase) may lead to adverse effects, it is critical to assess compound specificity. However, the problem has been that most "off-target" interactions are not predictable and the development of conventional experimental activity assays for kinases is very time consuming and resource intensive. As a result, even though compound specificity is critically important to assess, it has been extremely difficult, if not impossible, to do so comprehensively and systematically. Protein kinases are key regulators of most cellular signaling pathways in eukaryotic cells. Many protein kinase inhibitors have been developed to study specific functions of kinases in signaling pathways and as potential therapeutic agents (Cohen, P. (2002) Nat. Rev. Drug Discov. 1, 309-315) Because of the large size of the protein kinase superfamily (>500 human) and the fact that most kinase inhibitors bind in the highly conserved ATP-binding pocket, it is widely accepted that kinase inhibitors inhibit more than one target (Davies, S. P., Reddy, H., Caivano, M. & Cohen, P. (2000) Biochem. J. 351, 95-105). As a result, the inhibitors used as chemical tools to probe the often poorly understood roles of kinases in signaling pathways are paradoxically of incompletely characterized specificity. The same is true for kinase activators. The present invention is also usable for the parallel profiling of kinase activators of multiple kinases in one cavity.

PREFERRED EMBODIMENTS OF THE INVENTION

The difficulties noted above are solved by an assays format that allows testing many compounds against a very large panel of human kinases (up to 100 in one cavity). The assay makes it possible to assess specificity efficiently, quantitatively, comprehensively, and systematically. It is no longer necessary to grossly estimate compound specificity based on tests against only a small number of kinases. Specificity profiling can be incorporated earlier in the drug development process and along the entire development path, and specificity can be assessed systematically and rapidly for many more compounds. This unprecedented ability allows for tight feedback between medicinal chemistry and molecule testing. Potency and specificity can be optimized in parallel, leading to higher quality preclinical candidates in far less time.

Evaluating specificity comprehensively for existing late-stage candidates or drugs may also reveal previously unknown targets for these proven compounds. In some cases, the identification of new targets can suggest new indications, and in other cases may reveal the causes of side-effects that are not explained by the known, primary targets.

The subject matter of the invention is a novel approach to specificity profiling addresses one of the major bottlenecks in the development of small molecule kinase inhibitors or activators, and promises to have a major impact on the development of this important class of new drugs.

The subject matter of the invention is an assay that combines the Sandwich-ELISA (enzyme-linked immunosorbent assay) technique for the detection of autophosphorylation of tyrosine kinases with the Luminex™-xMAP detection system for the identification of particular proteins in a protein mixture like a cell lysate. The assay allows detecting the presence or absence of autophosphorylation of RTKs or NTKs in presence of a potential kinase inhibitor for up to 100 different kinases from e.g. a cell lysate in one cavity. The assay format allows the profiling of a potential kinase inhibitor for up to 100 different tyrosine kinases, by detecting the phosphorylation status with an anti phosphotyrosine antibody in one cavity. For example the assay allows performing a profiling in a Sandwich-ELISA in a 96 well plate for 96 different potential kinase inhibitors from an HTS against up to 100 kinases per well. An assay for measuring activation (i.e., autophosphorylation) of a tyrosine kinase receptor of interest is described in EP0730740 and comprise the following steps:

a) A first solid phase is coated with a substantially homogeneous population of cells from cell culture or animal material so that the cells adhere to the first solid phase. The cells have either an endogenous tyrosine kinase or have been transformed with DNA encoding a tyrosine kinase and the DNA has been expressed so that the tyrosine kinase construct is presented in the cell membranes or in the cytosol of the cells. b) A ligand is then added to the solid phase having the adhering cells, such that the tyrosine kinase is exposed to the ligand. c) Following exposure to the ligand, the adherent cells are solubilized, thereby releasing cell lysate. d) A second solid phase is coated with a capture agent as a specific antibody, which binds specifically to the tyrosine kinase, or, in the case of a receptor construct, to a polypeptide epitope tag. e) The cell lysate obtained in step c) is added to the wells containing the adhering capture agent so as to capture the tyrosine kinase to the wells. f) A washing step is then carried out, so as to remove unbound cell lysate, leaving the captured tyrosine kinase. g) The captured tyrosine kinase construct is exposed to a labelled anti-phosphotyrosine antibody which identifies phosphorylated residues in the tyrosine kinase. h) Binding of the anti-phosphotyrosine antibody to the captured tyrosine kinase is measured. The capture agent used in the present invention that allows the parallel detection of the autophosphorylation status of up to 100 tyrosine kinases in one well was derived from the Luminex™-xMap technology. The capture agent can be a binding protein coated bead or microsphere. The binding protein will most typically be a biomolecule such as a protein or a polynucleotide. The biomolecule may optionally be a naturally occurring, recombinant, or synthetic biomolecule. Antibodies or antibody fragments are highly suitable as protein-capture agents. The binding protein can also be an aptamer or antikalin or any other binding molecule. The Luminex™-xMap technology is a proven multiplex platform that uses precise ratios of two fluorescent dyes to create 100 different bead or microsphere sets that caries each another dye characterized by the ratios of two fluorescent dyes. Each set is distinguished based on his internal fluorescent dye ratio of two different dyes and can therefore bind an unique biological reagent as a specific antibody or monoclonal antibody against a particular tyrosine kinase. Antibodies bound to bead or microsphere surfaces serve as capture reagent in the sandwich ELISA test mentioned previously. Each antibody specific for different kinase bound to a bead surface with different fluorescent dyes ratio that results in a different color for each specific antibody-microsphere complex. The fluorescence color can be allocated to particular kinase that serves as antigen for the specific antibody that recognizes and binds a particular epitope of a definite kinase.

A phospho-specific antibody that recognizes phosphorylated tyrosine in general was used for the measurement of the autophoshorylation of the tyrosine kinases. The phospho-specific antibody is biotinylated and can be detected by a streptavidin coupled second fluorescence label (e.g. Phycoerythrin) that can be distinguished from the fluorescent dyes of the microsphers.

Phospho-specific antibodies are widely commercially available (e.g. from Cell Signaling Technology, Inc.; BioSource, Inc.; Santa Cruz; Biotechnology, Inc.; Upstate Biotechnology, Inc.), and may also be produced by techniques well known in the art.

The autophosphorylation of each captured kinase is analyzed by an instrument that is able to detect all unique fluorescent dyes colored microspheres and the streptavidin coupled fluorescence marker that binds the biotinylated anti phosphotyrosine antibody. These instruments are well known in the prior art. A Luminex™ instrument detects the different fluorescents reporter signals. In the Luminex™ instrument, the beads pass rapidly through two laser beams where high-speed digital signal processors distinguish between beads with two fluorescent signals (signal from microsphere and anti phosphotyrosine antibody signal) or one fluorescent signal (only signal from microsphere). In case of an autophosphorylation event, the phospho-specific antibody is able to bind the phosphorylated kinase that is captured by the specific antibody associated with a particular bead and two fluorescent signals can be detected. In case of lacking an autophosphorylation event only the microsphere signal is detectable by the laser.

All kinases in the test cell lysate that are inhibited by an added particular kinase inhibitor that will block autophosphorylation show only the microsphere signal and can be recognized as an tyrosine kinase that is inhibited by the kinase inhibitor tested. The kinase inhibitor tested does not inhibit kinases that show both signals. In an identical control cell lysate without kinase inhibior, kinases that have shown only one signal in the test lysate show both signals (signal from microsphere and anti phosphotyrosine antibody signal). These kinases are the group of kinases in the cell lysate, which are inhibited by the particular inhibitor tested.

The activation of kinases in cells is a well-known technique that is widely used in tissue culture laboratories. Depletion of fetal calf serum or other sera will starve cells. After starvation adding fetal calf serum (FCS) or other sera induces the activation of kinases. The activation can also be induced by growth factors and cytokines as e.g. EGF, VEGF, PDGF, HGF, TGF, NGF, FGF, insulin, various interleukines, and interferon. The growth factors and cytokines have to be applied as a cocktail for the induction of multiple kinases. The activation results in autophosphorylation of different kinases.

In another aspect of the invention the kinases are directly coupled to a microsphere. These coupling can be achieved by a fusionprotein like glutathion-s-transferase, when the microsphere is coated with glutathion or by an anti histidine antibody in case of coating with a 6× histidine tag. After coupling a kinase autophosphorylation reaction in presence of ATP takes place.

The main embodiment of the invention is a method for measuring the autophosphorylation of one or more tyrosine kinases in presence of a kinase inhibitor compared to the absence of said kinase inhibitor, the method comprising the steps:

(a) starving cells by serum depletion,
(b) inducing of kinase autophosphorylation activity by adding serum, growth factors and/or cytokines in presence and in absence of a kinase inhibitor,
(c) solubilizing the cells thereby releasing cell lysate therefrom,
(d) capturing the kinases in the cell lysate by adding different tyrosine kinase specific binding protein, wherein each different binding protein is associated with an unique dye,
(e) adding a phosphotyrosine specific antibody tagged with a marker distinguishable from any of the unique dyes from d) and
(f) identifying the autophosphorylated tyrosine kinases that have unique dyes from d) and the marker from the phosphotyrosine specific antibodies from e),
(g) comparing the autophosphorylated tyrosine kinases from f) resulting from an induction in presence of a kinase inhibitor with the induction in absence of said kinase inhibitor.

A variation thereof is a method for measuring the autophosphorylation of one or more tyrosine kinases in presence of a kinase inhibitor compared to the absence of said kinase inhibitor, the method comprising the steps:
(a) coupling of definite tyrosine kinase to a unique dye,
(b) kinase reaction in presence and in absence of a kinase inhibitor,
(c) adding a phosphotyrosine specific antibody tagged with a marker distinguishable from any of the unique dyes from a) and
(d) identifying the autophosphorylated tyrosine kinases that have unique dyes from a) and the marker from the phosphotyrosine specific antibodies from c),
(e) comparing the autophosphorylated tyrosine kinases from d) resulting from an induction in presence of a kinase inhibitor with the induction in absence of said kinase inhibitor.

The used dyes are preferable but not limited fluorescence or luminescence dyes.

In another embodiment of the invention a transformation prior to cell starvation, with a nucleic acid encoding a polypeptide of a protein that is able to induce phosphorylation in the cells.

The cells can be eukaryotic cells and in a preferred embodiment the cells are mammalian cells.

Another aspect of the invention is a composition containing 1-100 unique dyes each associated with one different capture anti tyrosine kinase antibody which binds specifically to a definite tyrosine kinase which has an epitope to which the capture antibody can specifically bind, for the measurement of autophosphorylation from 1-100 different kinases in parallel.

The number unique dyes can be between 1 and 100 for the measurement of autophosphorylation from 1-100 different kinases in parallel.

A preferred number of kinases that can be measured in parallel are between 1-20, 1-40, 1-60 and 1-80 kinases.

A further embodiment of the invention is a kit for use in a method mentioned above for profiling the specificity of kinase inhibitors comprising:
(a) a composition of 1-100 unique dyes associated with a different capture anti tyrosine kinase antibody which binds specifically to a definite tyrosine kinase which has an epitope to which the capture antibody can specifically bind; and,
(b) an anti phosphotyrosine antibody labeled with a dye distinguishable from the dyes in a).

The method, the kit and the composition can be used for the specificity profiling of each potential kinase inhibitor by measurement of autophosphorylation from 1-100 different kinases in parallel in presence of the kinase inhibitor in comparison to measurement of autophosphorylation from 1-100 different kinases in parallel in absence of the kinase inhibitor. A Luminex™ instrument can be used for the measurement of autophosphorylation. The kinase inhibitor can inhibit kinases that show autophosphorylation only in absence of the kinase inhibitor.

The method can be performed in a microtiter plate.

Another use for the method of the invention is the profiling of the auto phosphorylation status of various kinases in tumor specimen. The status of activity from various kinases gives a reflective hint for the diagnosis and the suitable therapeutic strategy to cure the patient (Espina V. et al. (2005) Cancer Invest, 23(1), pp. 36-46). In this particular case the sample that has to be analyzed would be a protein supernatant or a lysate from a tumor specimen (biopsies or laser capture micro dissection), a blood sample or animal materiel. The analysis can be done as described above in absence of a kinase inhibitor.

Figure 1:
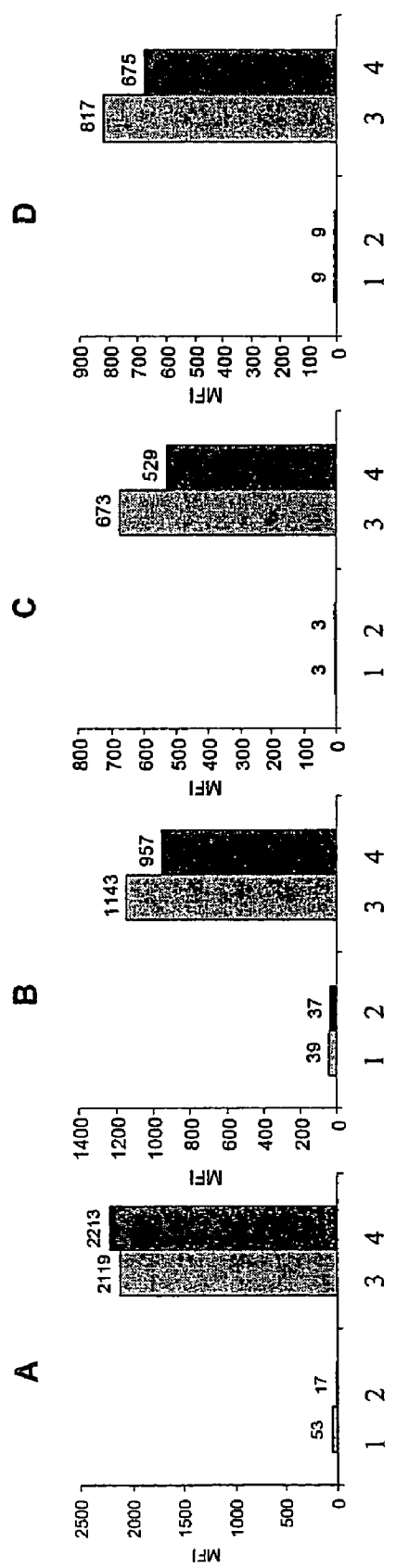
FIG. 1 shows the results of four independent experiments (A: EGFR-phosphorylation; B: FAK-phosphorylation; C: IGFR1-phosphorylation and D: Met-phosphorylation). The autophosphorylation was detected by the measurement of the mean fluorescence intensity (MFI). The columns show the MFI rates for the following experimental set ups (bright grey are set-ups with multiple capture antibodies coupled with fluorescence dye microspheres in one cavity, dark grey are set-ups with a single capture antibodies coupled with fluorescence dye microspheres in one cavity.

Column A1 (MFI=53)
capture antibodies for EGFR coupled with fluorescence dye microspheres,
capture antibodies for IGFR coupled with fluorescence dye microspheres,
capture antibodies for FAK coupled with fluorescence dye microspheres,
capture antibodies for Met coupled with fluorescence dye microspheres,
EGF-Kinase inhibitor and
EGF
Column A2 (MFI=17)
capture antibodies for EGFR coupled with fluorescence dye microspheres,
EGF-Kinase inhibitor and
EGF
Column A3 (MFI=2119)
capture antibodies for EGFR coupled with fluorescence dye microspheres,
capture antibodies for IGFR coupled with fluorescence dye microspheres,
capture antibodies for FAK coupled with fluorescence dye microspheres,
capture antibodies for Met coupled with fluorescence dye microspheres and
EGF
Column A4 (MFI=2213)
capture antibodies for EGFR coupled with fluorescence dye microspheres and EGF
Column B1 (MFI=39)
capture antibodies for EGFR coupled with fluorescence dye microspheres, capture antibodies for IGFR coupled with fluorescence dye microspheres,
capture antibodies for FAK coupled with fluorescence dye microspheres,
capture antibodies for Met coupled with fluorescence dye microspheres,
FAK-Kinase inhibitor and
FCS
Column B2 (MFI=37)
capture antibodies for FAK coupled with fluorescence dye microspheres,
FAK-Kinase inhibitor and
FCS
Column B3 (MFI=1143)
capture antibodies for EGFR coupled with fluorescence dye microspheres,
capture antibodies for IGFR coupled with fluorescence dye microspheres,
capture antibodies for FAK coupled with fluorescence dye microspheres,
capture antibodies for Met coupled with fluorescence dye microspheres and
FCS
Column B4 (MFI=957)
capture antibodies for FAK coupled with fluorescence dye microspheres and
FCS
Column C1 (MFI=3)
capture antibodies for EGFR coupled with fluorescence dye microspheres,
capture antibodies for IGFR coupled with fluorescence dye microspheres,
capture antibodies for FAK coupled with fluorescence dye microspheres,
capture antibodies for Met coupled with fluorescence dye microspheres,
IGFR1—Kinase inhibitor and
IGF
Column C2 (MFI=3)
capture antibodies for IGFR1 coupled with fluorescence dye microspheres,
IGFR1—Kinase inhibitor and
IGF
Column C3 (MFI=673)
capture antibodies for EGFR coupled with fluorescence dye microspheres,
capture antibodies for IGFR coupled with fluorescence dye microspheres,
capture antibodies for FAK coupled with fluorescence dye microspheres,
capture antibodies for Met coupled with fluorescence dye microspheres and
IGF
Column C4 (MFI=529)
capture antibodies for FAK coupled with fluorescence dye microspheres and
IGF
Column D1 (MFI=9)
capture antibodies for EGFR coupled with fluorescence dye microspheres,
capture antibodies for IGFR coupled with fluorescence dye microspheres,
capture antibodies for FAK coupled with fluorescence dye microspheres,
capture antibodies for Met coupled with fluorescence dye microspheres,
Met-Kinase inhibitor and
HGF
Column D2 (MFI=9)
capture antibodies for Met coupled with fluorescence dye microspheres,
Met-Kinase inhibitor and
HGF
Column D3 (MFI=817)
capture antibodies for EGFR coupled with fluorescence dye microspheres,
capture antibodies for IGFR coupled with fluorescence dye microspheres,
capture antibodies for FAK coupled with fluorescence dye microspheres,
capture antibodies for Met coupled with fluorescence dye microspheres and
HGF
Column D4 (MFI=675)
capture antibodies for Met coupled with fluorescence dye microspheres and
HGF

FIG. 2

Section A

Measurement of autophosphorylation of EGFR (-♦-), FAK (-■-), IGFR1 (-▲-) and Met (-○-) in % of positive control (100%=autophosphorylation of EGFR upon EGF activation in absence of an EGFR inhibitor)

Co stimulation with EGF, IGF and HGF in presence of increasing concentrations of an EGFR inhibitor (as indicated).

Section B

Measurement of autophosphorylation of EGFR (-♦-), FAK (-■-), IGFR1 (-▲-) and Met (-○-) in % of positive control (100%=autophosphorylation of IGFR1 upon IGF activation in absence of an IGFR1 inhibitor)

Co stimulation with EGF, IGF and HGF in presence of increasing concentrations of an IGF1R inhibitor (as indicated).

Section C

Measurement of autophosphorylation of EGFR (-♦-), FAK (-■-), IGFR1 (-▲-) and Met (-○-) in % of positive control (100%=autophosphorylation of Met upon HGF activation in absence of a Met inhibitor)

Co stimulation with EGF, IGF and HGF in presence of increasing concentrations of a Met inhibitor (as indicated).

FIG. 3

Section A

Measurement of autophosphorylation of FGFR1 (1), FGFR2 (2), FGFR3 (3), IGF1R (4), Met (5), CSF1R (6) catalytic domains coupled with fluorescence dye microspheres in increasing concentrations of PTK787 kinase inhibitor concentration in % of positive control (100%=autophosphorylation without kinase inhibitor (only DMSO).

Section B

Measurement of autophosphorylation of InsR (1), VEGFR1 (2), FGFR4 (3), PDGFRA (4), PDGFRB (5), Fak (6), Tyk (7), EGFR (8) catalytic domains coupled with fluorescence dye microspheres in increasing concentrations of PTK787 kinase inhibitor concentration in % of positive control (100%=autophosphorylation without kinase inhibitor (only DMSO).

Section C

Measurement of autophosphorylation of Tie2 (1), NTRK1 (2), Axl (3), VEGFR2 (4), Tek (5), Ros1 (6) catalytic domains coupled with fluorescence dye microspheres in increasing concentrations of PTK787 kinase inhibitor concentration in % of positive control (100%=autophosphorylation without kinase inhibitor (only DMSO).

EXAMPLES

Example 1

Cell Culture, Inhibitor Treatment and Cell Lyses

Human tumor cell line HT29 (colorectal carcinoma) were obtained from ATCC and maintained in Dulbecco's modified Eagle's medium containing 10% fetal calf serum at 37° C. in 5% $CO_2$. 16-20 h before inhibitor treatment HT29 cells were starved in medium without fetal calf serum. Cells were incubated for 45 min with 30 µM kinase inhibitor (EGFR-lnhibitor, FAK-inhibitor, IGFR1-inhibitor or Met-Inhibitor) or in medium without kinase inhibitor as a positive control.

The kinases inhibitors are (3-Chloro-4-fluoro-phenyl)-[7-methoxy-6-(3-morpholin-4-yl-propoxy)-quinazolin-4-yl]-amine (Iressa) for EGFR, 5-(2,6-Dichloro-phenylmethanesulfonyl)-3-[1-[3,5-dimethyl-4-((R)-2-pyrrolidin-1-ylmethyl-pyrrolidine-1-carbonyl)-1H-pyrrol-2-yl]-meth-(Z)-ylidene]-1,3-dihydro-indol-2-one (PHA 665752, Christensen et al. (2003) Cancer Res. (63), pp. 7345-7355) for Met and $N^4$-Quinolin-3-yl-$N^2$-(3,4,5-trimethoxy-phenyl)-pyrimidine-2,4-diamine for FAK and IGFR1.

Activation of the kinases was initiated for 10-15 min with 100 ng/ml of the corresponding ligands EGF, IGF, HGF for Met kinase or fetal calf serum (FCS) for FAK kinase. Cells were washed with ice-cold TBS and lysed with 1% NP40 in 20 mM Tris-HCl pH 8.0, 150 mM NaCl supplemented with 10% Glycerol, 1% Phosphatase Inhibitor Cocktail I (Sigma), 1% Phosphatase Inhibitor Cocktail II (Sigma), 0.1% Protease Inhibitor Cocktail III (Calbiochem), 0.01% Benzonase (Novagen) for 20 min on ice.

Luminex™ Bead Assay $2.5\times10^6$ Luminex microspheres were coupled with 50 µg/ml antibody as described by the manufacturer (capture antibodies for EGFR, IGFR, MET and Fak were obtained from R&D-Systems and Upstate). 1000 antibody-coupled microspheres per well were incubated with HT29 cell lysates in assay buffer (Blocking reagent, Roche, 1% Tween 20) over night at 4° C. with agitation. After three wash steps with assay buffer, phosphorylated tyrosin-residues were detected with a biotinylated anti-phospho-tyrosin antibody (1 h agitation at room temperature; Santa Cruz Biotechnology) and phycoerythrin-conjugated Streptavidin (45 min agitation at room temperature; Dianova). Microspheres were analysed in a Luminex™ 100 machine as described by the manufacturer.

For testing the measurement of autophosphorylation in single experiments or in parallel experiments with or without a suitable kinase inhibitor in one cavity the following set-ups were tested (see also FIG. 1).

A1
capture antibodies for EGFR coupled with fluorescence dye microspheres,
capture antibodies for IGFR coupled with fluorescence dye microspheres,
capture antibodies for FAK coupled with fluorescence dye microspheres,
capture antibodies for Met coupled with fluorescence dye microspheres,
EGF-Kinase inhibitor and
EGF
A2
capture antibodies for EGFR coupled with fluorescence dye microspheres,
EGF-Kinase inhibitor and
EGF
A3
capture antibodies for EGFR coupled with fluorescence dye microspheres,
capture antibodies for IGFR coupled with fluorescence dye microspheres,
capture antibodies for FAK coupled with fluorescence dye microspheres,
capture antibodies for Met coupled with fluorescence dye microspheres and
EGF
A4
capture antibodies for EGFR coupled with fluorescence dye microspheres and
EGF
B1
capture antibodies for EGFR coupled with fluorescence dye microspheres,
capture antibodies for IGFR coupled with fluorescence dye microspheres,
capture antibodies for FAK coupled with fluorescence dye microspheres,
capture antibodies for Met coupled with fluorescence dye microspheres,
FAK-Kinase inhibitor and
FCS
B2
capture antibodies for FAK coupled with fluorescence dye microspheres,
FAK-Kinase inhibitor and
FCS
B3
capture antibodies for EGFR coupled with fluorescence dye microspheres,
capture antibodies for IGFR coupled with fluorescence dye microspheres,
capture antibodies for FAK coupled with fluorescence dye microspheres,
capture antibodies for Met coupled with fluorescence dye microspheres and
FCS
B4
capture antibodies for FAK coupled with fluorescence dye microspheres and
FCS
capture antibodies for EGFR coupled with fluorescence dye microspheres,
capture antibodies for IGFR coupled with fluorescence dye microspheres,
capture antibodies for FAK coupled with fluorescence dye microspheres,
capture antibodies for Met coupled with fluorescence dye microspheres,
IGFR1—Kinase inhibitor and
IGF
C2
capture antibodies for IGFR1 coupled with fluorescence dye microspheres,
IGFR1—Kinase inhibitor and
IGF
C3
capture antibodies for EGFR coupled with fluorescence dye microspheres,
capture antibodies for IGFR coupled with fluorescence dye microspheres,
capture antibodies for FAK coupled with fluorescence dye microspheres,
capture antibodies for Met coupled with fluorescence dye microspheres and IGF
C4
capture antibodies for FAK coupled with fluorescence dye microspheres and
IGF
D1
capture antibodies for EGFR coupled with fluorescence dye microspheres,
capture antibodies for IGFR coupled with fluorescence dye microspheres,
capture antibodies for FAK coupled with fluorescence dye microspheres,
capture antibodies for Met coupled with fluorescence dye microspheres,
Met-Kinase inhibitor and
HGF
D2
capture antibodies for Met coupled with fluorescence dye microspheres,
Met-Kinase inhibitor and
HGF
D3
capture antibodies for EGFR coupled with fluorescence dye microspheres,
capture antibodies for IGFR coupled with fluorescence dye microspheres,
capture antibodies for FAK coupled with fluorescence dye microspheres,
capture antibodies for Met coupled with fluorescence dye microspheres and
HGF
D4
capture antibodies for Met coupled with fluorescence dye microspheres and
HGF Example 2

Cell Culture, Inhibitor Treatment and Cell Lyses

Figure 2:
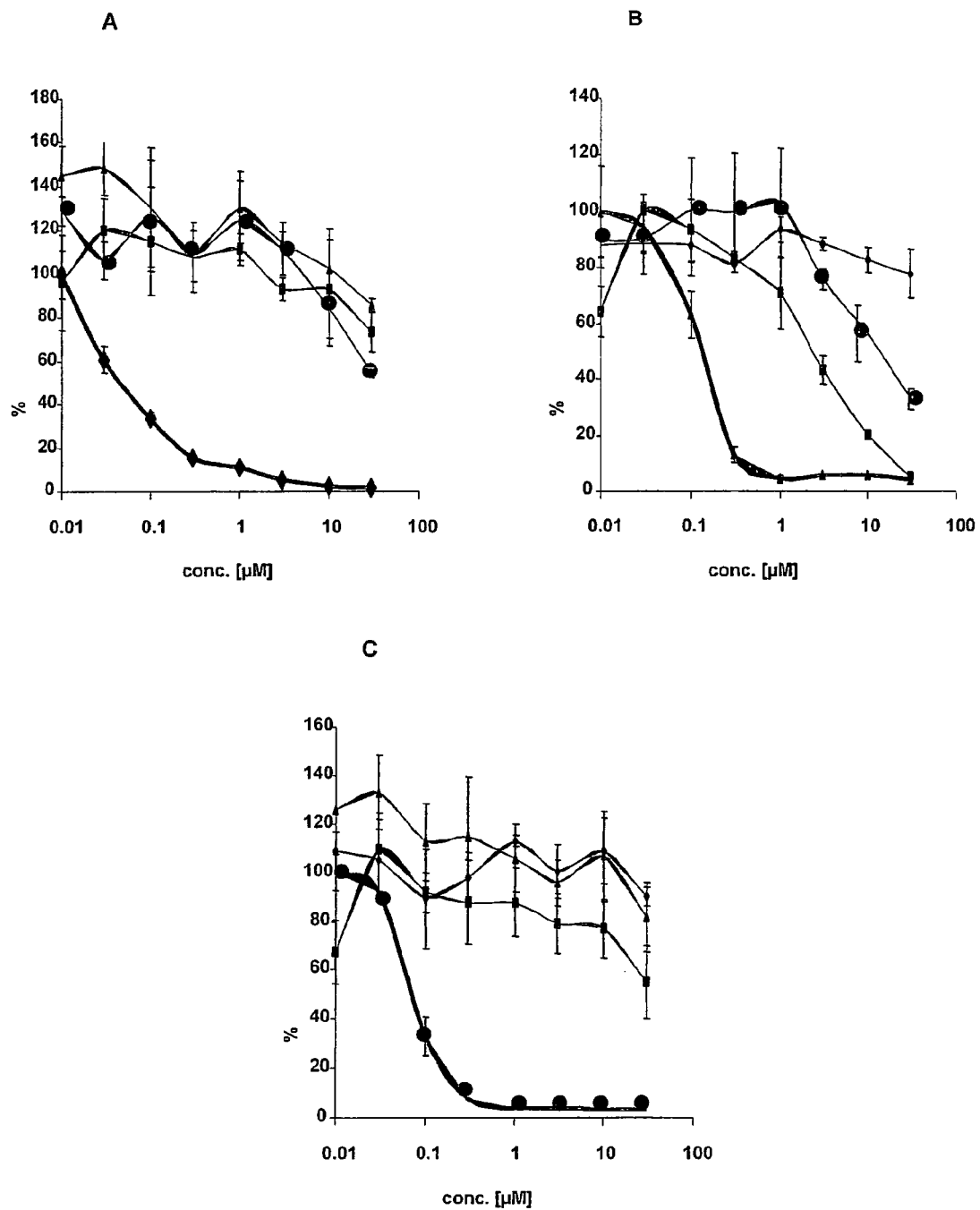

Human tumor cell line HT29 (colorectal carcinoma) were obtained from ATCC and maintained in Dulbecco's modified Eagle's medium containing 10% fetal calf serum at 37° C. in 5% $CO_2$. 16-20 h before inhibitor treatment HT29 cells were starved in medium without fetal calf serum. Cells were incubated for 45 min with different concentration of kinase inhibitor (0.01 μM; 0.03 μM, 0.1 μM; 0.3 μM, 1.0 μM, 3 μM, 10 μM, 30 μM, EGFR-Inhibitor [FIG. 2A], IGFR1-inhibitor [FIG. 2B] and Met-Inhibitor [FIG. 2C]). A positive control with DMSO without kinase inhibitors serves as reference kinase activity (100%).

The kinases inhibitors are (3-Chloro-4-fluoro-phenyl)-[7-methoxy-6-(3-morpholin-4-yl-propoxy)-quinazolin-4-yl]-amine (Iressa) for EGFR, 5-(2,6-Dichloro-phenylmethane-sulfonyl)-3-[1-[3,5-dimethyl-4-((R)-2-pyrrolidin-1-ylmethyl-pyrrolidine-1-carbonyl)-1H-pyrrol-2-yl]-meth-(Z)-ylidene]-1,3-dihydro-indol-2-one (PHA 665752, Christensen et al. (2003) Cancer Res. (63), pp. 7345-7355) for Met and $N^4$-Quinolin-3-yl-$N^2$-(3,4,5-trimethoxy-phenyl)-pyrimidine-2,4-diamine for IGFR1.

Activation of the kinase was initiated for 10-15 min with 10 ng/ml of EGF, IGF, HGF for Met kinase. Cells were washed with ice-cold TBS and lysed with 1% NP40 in 20 mM Tris-HCl pH 8.0, 150 mM NaCl supplemented with 10% Glycerol, 1% Phosphatase Inhibitor Cocktail I (Sigma), 1% Phosphatase Inhibitor Cocktail II (Sigma), 0.1% Protease Inhibitor Cocktail III (Calbiochem), 0.01% Benzonase (Novagen) for 20 min on ice.

Luminex™ Bead Assay $2.5 \times 10^6$ Luminex microspheres were coupled with 50 μg/ml antibody as described by the manufacturer (The capture antibody for EGFR, IGFR, MET and FAK were obtained from R&D-Systems and Upstate). 1000 antibody-coupled microspheres per well were incubated with HT29 cell lysates in assay buffer (Blocking reagent, Roche, 1% Tween 20) over night at 4° C. with agitation. After three wash steps with assay buffer, phosphorylated tyrosin-residues were detected with a biotinylated anti-phospho-tyrosin antibody (1 h agitation at room temperature; Santa Cruz Biotechnology) and phycoerythrin-conjugated Streptavidin (45 min agitation at room temperature; Dianova). Microspheres were analysed in a Luminex™100 machine as described by the manufacturer.

Example 3

Constructs, Cell Culture and Cell Lyses

The catalytic domain of InsR, VEGFR1, FGFR4, PDGFRA, PDGFRB, Fak, Tyk, EGFR, FGFR1, FGFR2, FGFR3, IGF1R, Met, CSF1R, Tie2, NTKRK1, Axl, VEGFR2, Tek, Ros1 tyrosinkinase were subcloned into vector pIEX1 (Novagen) for the expression with a N-terminal 6×His-affinity-Tag and S-Tag. Hi5 Insect cells (BTI-TN-5B1-4; Invitrogen) were maintained in Express Five SFM medium (Invitrogen) with 18 mM Glutamine, 50 U/ml Penicillin and 50 μg/ml Streptomycin at 27° C. $1 \times 10^6$ Hi5 insect cells were transiently transfected with 2 μg DNA and 10 μl Gene Juice transfection reagent (Novagen) as described by the manufacturer. 48 h post transfection cells were washed with ice-cold TBS and lysed with 1% NP40 in 20 mM Tris-HCl pH 8.0, 150 mM NaCl supplemented with 1% Phosphatase Inhibitor Cocktail I (Sigma), 1% Phosphatase Inhibitor Cocktail II (Sigma), 0.1% Protease Inhibitor Cocktail III (Calbiochem), 0.01% Benzonase (Novagen) for 15 min on ice. Lysates were centrifuged with 33600×g for 45 minutes. Supernatants were used immediately or were shock-frozen with 30% glycerol.

Luminex Bead Assay 0.5 μl Ni-NTA-Luminex microspheres (Qiagen) were coupled with cell lysat from recombinant protein expression for 60 min at 4° C. as described by the manufacturer. Each catalytic domain of a particular kinase was coupled with a particular distinguishable microsphere. Kinase autophosphorylation reaction was started with 5 μM ATP and 40 mM MgCl2 in assay buffer (20 mM MOPS, 25 mM β-glycerophosphate, 5 mM EGTA, 1 mM DTT, 1 mM sodiumvanadate, ph 7,2 supplemented with 0.1% BSA and 0.03% Brij35) for 30 min at 37° C. with agitation. The kinase autophosphorylation reaction was performed in presence of 10 μM, 3 μM, 1 μM, 0.3 μM, 0.1 μM, 0.03 μM kinase inhibitor (PTK787) or in absence of a kinase inhibitor as positive control (only DMSO). The kinase reaction was stopped with 150 mM EDTA. After three wash steps with Detection buffer (1% BSA, 0.03% Brij35 in PBS, phosphorylated tyrosin-residues were detected with a biotinylated anti-phospho-tyrosine antibody (1 h agitation at room temperature; Santa Cruz Biotechnology) and phycoerythrin-conjugated streptavidin (45 min agitation at room temperature; Dianova). Microspheres were analysed in a Luminex[100] machine as described by the manufacturer.

Figure 3:
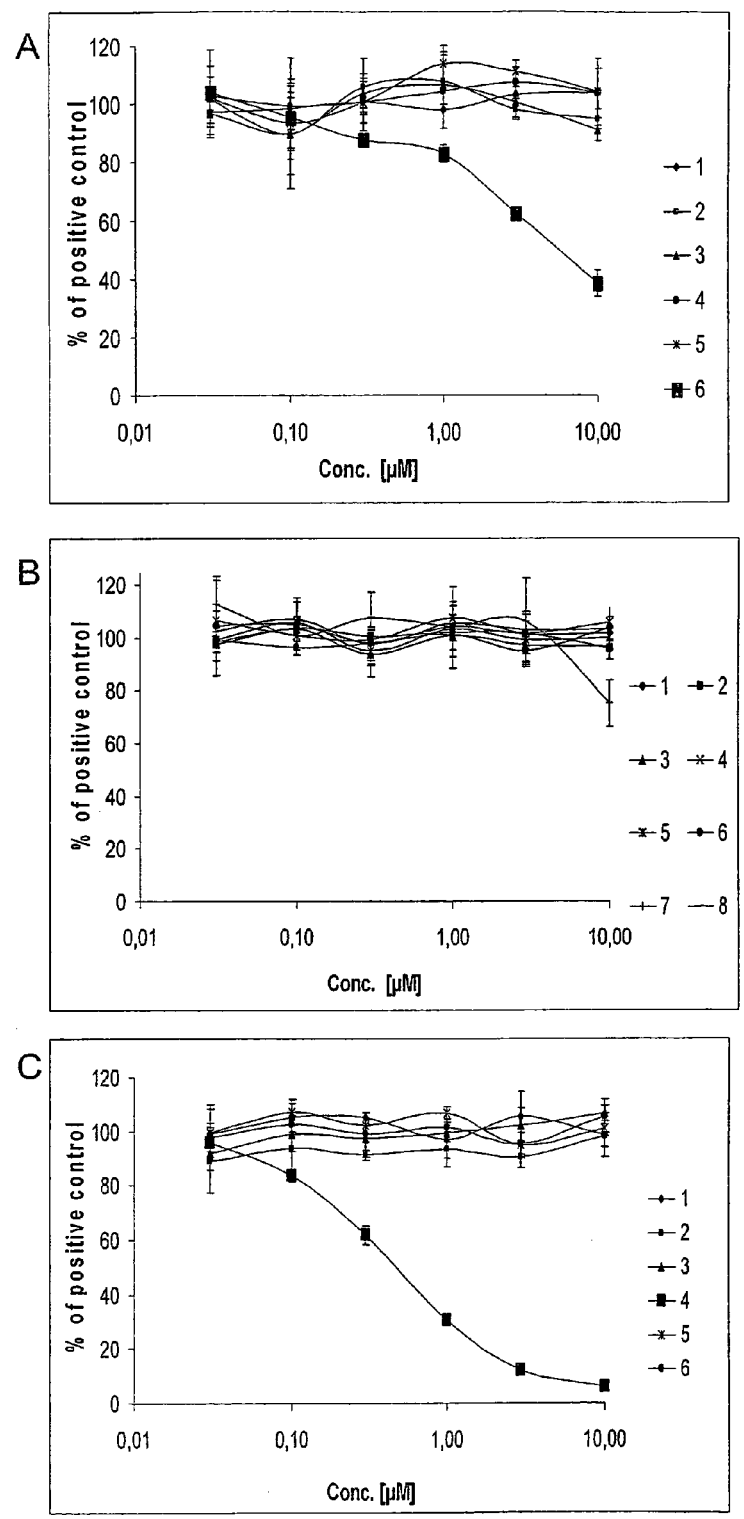

For testing the measurement of autophosphorylation in parallel experiments with PTK 787 inhibitor in one cavity the following set-ups were tested (see also FIG. 3).

A
graph 1: FGFR1 (catalytic domain) coupled with fluorescence dye microspheres,
graph 2: FGFR2 (catalytic domain) coupled with fluorescence dye microspheres
graph 3: FGFR3 (catalytic domain) coupled with fluorescence dye microspheres
graph 4: IGF1R (catalytic domain) coupled with fluorescence dye microspheres
graph 5: Met (catalytic domain) coupled with fluorescence dye microspheres
graph 6: CSF1R (catalytic domain) coupled with fluorescence dye microspheres
B
graph 1: InsR (catalytic domains) coupled with fluorescence dye microspheres,
graph 2: VEGFR1 (catalytic domain) coupled with fluorescence dye microspheres
graph 3: FGFR4 (catalytic domain) coupled with fluorescence dye microspheres
graph 4: PDGFRA (catalytic domain) coupled with fluorescence dye microspheres
graph 5: PDGFRB (catalytic domain) coupled with fluorescence dye microspheres
graph 6: Fak (catalytic domain) coupled with fluorescence dye microspheres
graph 7: Tyk (catalytic domain) coupled with fluorescence dye microspheres
graph 8: EGFR (catalytic domain) coupled with fluorescence dye microspheres
C
graph 1: Tie2 (catalytic domain) coupled with fluorescence dye microspheres,
graph 2: NTRK1 (catalytic domain) coupled with fluorescence dye microspheres
graph 3: Axl (catalytic domain) coupled with fluorescence dye microspheres
graph 4: VEGFR2 (catalytic domain) coupled with fluorescence dye microspheres
graph 5: Tek (catalytic domain) coupled with fluorescence dye microspheres
graph 6: Ros1 (catalytic domain) coupled with fluorescence dye microspheres

We claim:

1. A method for measuring autophosphorylation of a tyrosine kinase in presence of a kinase inhibitor compared to autophosphorylation of said tyrosine kinase in absence of said kinase inhibitor, comprising
    (a) starving cells by serum depletion,
    (b) inducing kinase autophosphorylation activity by adding serum, growth factors and/or cytokines in presence and in absence of a kinase inhibitor,
    (c) solubilizing the cells to release a cell lysate,
    (d) capturing the tyrosine kinase in the cell lysate by adding a plurality of tyrosine kinase specific binding proteins, wherein each binding protein is associated with a unique dye,
    (e) adding a phosphotyrosine specific antibody tagged with a marker, wherein said marker is distinguishable from any of the unique dyes from d),
    (f) identifying the autophosphorylated tyrosine kinase by detecting the unique dye from d) and the marker from e), and
    (g) comparing a level of autophosphorylation of said tyrosine kinase in the presence of said kinase inhibitor to a level of autophosphorylation of said tyrosine kinase in the absence of said kinase inhibitor,
    wherein in case of autophosphorylation, a first signal for said unique dye and a second signal for said marker are detected whereas in case of lack of autophosphorylation, only the first signal for the unique dye is detected.

2. The method of claim 1 wherein the dye is a fluorescence or luminescence dye.

3. The method of claim 1 wherein the marker is a fluorescence or luminescence marker.

4. A method of claim 1 wherein the cells are transformed prior to cell starvation in step (a), with a nucleic acid encoding a polypeptide or a protein that induces phosphorylation in said cells.

5. The method of claim 1 wherein the cells are eukaryotic cells.

6. The method of claim 5 wherein the eukaryotic cells are mammalian cells.

7. The method according to claim 1, wherein the tyrosine kinase is epidermal growth factor receptor (EGFR), PDGF receptor, insulin receptor tyrosine kinase (IRK), Met receptor tyrosine kinase, fibroblast growth factor (FGF) receptor, insulin receptor, insulin growth factor (IGF-1) receptor, TrkA receptor, TIE-1, Tek/Tie2, Flt-1, Flk, VEGFR3, EGFR (HER-1, ERBB2 (HER-2), ERBB3 (HER-3), ERBB4 (HER-4), Ret, Kit, Alk, Axl1, FGFR1, FGFR2, FGFR3 or an Eph receptor.

8. The method according to claim 1, wherein the binding protein is an antibody, an aptamer or an antikalin molecule.

9. The method according to claim 1, wherein the binding protein is coated onto a microsphere or bead.

10. The method according to claim 1, wherein the antibody is a phospho-specific antibody that recognizes phosphorylated tyrosine.

11. A method for measuring autophosphorylation of a tyrosine kinase in presence of a kinase inhibitor compared to autophosphorylation of said tyrosine kinase in absence of said kinase inhibitor, comprising
    (a) coupling a specific tyrosine kinase to a unique dye,
    (b) conducting a kinase reaction in the presence and in the absence of a kinase inhibitor,
    (c) adding a phosphotyrosine specific antibody tagged with a marker, wherein said marker is distinguishable from the unique dye from a),
    (d) identifying the autophosphorylated tyrosine kinase by detecting the unique dye from a) and the marker from c),
    (e) comparing a level of autophosphorylation of said tyrosine kinase in the presence of said kinase inhibitor to a level of autophosphorylation of said tyrosine kinase in the absence of said kinase inhibitor,
    wherein in case of autophosphorylation, a first signal for said unique dye and a second signal for said marker are detected whereas in case of lack of autophosphorylation, only the first signal for the unique dye is detected.

12. A method for measuring autophosphorylation of a tyrosine kinase in presence of a kinase activator compared to autophosphorylation of said tyrosine kinase in absence of said kinase activator, comprising
    (a) starving cells by serum depletion,
    (b) inducing kinase autophosphorylation activity by adding serum, growth factors and/or cytokines in presence and in absence of a kinase activator,
    (c) solubilizing the cells to release a cell lysate,
    (d) capturing the tyrosine kinase in the cell lysate by adding a plurality of tyrosine kinase specific binding proteins, wherein each binding protein is associated with a unique dye, (e) adding a phosphotyrosine specific antibody tagged with a marker, wherein said marker is distinguishable from any of the unique dyes from d), (f) identifying the autophosphorylated tyrosine kinase by detecting the unique dye from d) and the marker from e), and (g) comparing a level of autophosphorylation of said tyrosine kinase in the presence of said kinase activator to a level of autophosphorylation of said tyrosine kinase in the absence of said kinase activator, wherein in case of autophosphorylation, a first signal for said unique dye and a second signal for said marker are detected whereas in case of lack of autophosphorylation, only the first signal for the unique dye is detected.

13. A method for profiling kinase inhibitors for their specificity to inhibit a tyrosine kinase, comprising (a) starving cells by serum depletion, (b) inducing kinase autophosphorylation activity by adding serum, growth factors and/or cytokines in presence and in absence of a kinase inhibitor, (c) solubilizing the cells to release a cell lysate, (d) capturing the tyrosine kinase in the cell lysate by adding a plurality of tyrosine kinase specific binding proteins, wherein each binding protein is associated with a unique dye, (e) adding a phosphotyrosine specific antibody tagged with a marker, wherein said marker is distinguishable from any of the unique dyes from d), (f) identifying the autophosphorylated tyrosine kinase by detecting the unique dye from d) and the marker from e), and (g) comparing a level of autophosphorylation of said tyrosine kinase in the presence versus in the absence of said kinase inhibitor, wherein in case of lack of kinase inhibition, a first signal for said unique dye and a second signal for said marker are detected whereas in case of kinase inhibition, only the first signal for the unique dye is detected.

14. A method for profiling kinase activators for their specificity to activate tyrosine a tyrosine kinase, comprising (a) starving cells by serum depletion, (b) inducing kinase autophosphorylation activity by adding serum, growth factors and/or cytokines in presence and in absence of a kinase activator, (c) solubilizing the cells to release a cell lysate, (d) capturing the tyrosine kinase in the cell lysate by adding a plurality of tyrosine kinase specific binding proteins, wherein each binding protein is associated with a unique dye, (e) adding a phosphotyrosine specific antibody tagged with a marker, wherein said marker is distinguishable from any of the unique dyes from d), (f) identifying the autophosphorylated tyrosine kinase by detecting the unique dye from d) and the marker from e), and (g) comparing a level of autophosphorylation of said tyrosine kinase in the presence versus in the absence of said kinase inhibitor, wherein in case of kinase activation, a first signal for said unique dye and a second signal for said marker are detected whereas in case of lack of kinase activation, only the first signal for the unique dye is detected.

15. A method for diagnosis and staging of a tumor characterized by enhanced tyrosine kinase activity or over-expression thereof comprising profiling phosphorylation status of a tyrosine kinase in absence of a kinase inhibitor, said profiling comprising (a) starving cells by serum depletion, (b) inducing kinase autophosphorylation activity by adding serum, growth factors and/or cytokines in presence and in absence of a kinase inhibitor, (c) solubilizing the cells to release a cell lysate, (d) capturing the tyrosine kinase in the cell lysate by adding a plurality of tyrosine kinase specific binding proteins, wherein each binding protein is associated with a unique dye, (e) adding a phosphotyrosine specific antibody tagged with a marker, wherein said marker is distinguishable from any of the unique dyes from d), (f) identifying the autophosphorylated tyrosine kinase by detecting the unique dye from d) and the marker from e), and (g) comparing a level of autophosphorylation of said tyrosine kinase in the presence of said kinase inhibitor to a level of autophosphorylation of said tyrosine kinase in the absence of said kinase inhibitor wherein the lysates are obtained from tumor specimen, blood samples or animal material, wherein in case of autophosphorylation, a first signal for said unique dye and a second signal for said marker are detected whereas in case of lack of autophosphorylation, only the first signal for the unique dye is detected.

16. A method for measuring autophosphorylation of a tyrosine kinase in presence of a kinase inhibitor compared to autophosphorylation of said tyrosine kinase in absence of said kinase inhibitor, comprising (a) activating autophosphorylation of a plurality of tyrosine kinases in a serum-starved cell sample by adding serum, growth factors and cytokines, wherein said said tyrosine kinases are activated in the absence and in the presence of said kinase inhibitor;

(b) capturing a plurality of tyrosine kinases in a lysate of said cell sample from (a) with a plurality of tyrosine kinase-specific antibodies, wherein each specific antibody is conjugated to a unique dye and further binds specifically to a tyrosine kinase;

(c) adding a second phosphotyrosine-specific antibody tagged with a marker, wherein said marker is distinguishable from any of the unique dyes from (b);

(d) identifying the autophosphorylated tyrosine kinase by detecting both the unique dye from (b) and the marker from (c); and (e) comparing a level of autophosphorylation of said tyrosine kinase in the presence of said kinase inhibitor to level of autophosphorylation of said tyrosine kinase in the in the absence of said kinase inhibitor;

wherein in case of autophosphorylation, a first fluorescence signal for said unique dye and a second fluorescence signal for said marker are detected whereas in case of lack of autophosphorylation, only the first fluorescence signal for the unique dye is detected.

* * * * *